(12) United States Patent
Iwata et al.

(10) Patent No.: US 7,218,401 B2
(45) Date of Patent: May 15, 2007

(54) SURFACE PLASMON SENSOR, SURFACE PLASMON RESONANCE MEASUREMENT DEVICE, AND DETECTION CHIP

(75) Inventors: Yuji Iwata, Haguri-gun (JP); Takahiro Tohyama, Tokai (JP); Tsuneo Chinzei, Shinagawa-ku (JP); Hidemoto Nakagawa, Yokohama (JP); Isao Shimoyama, Nerima-ku (JP); Kiyoshi Matsumoto, Nakano-ku (JP)

(73) Assignee: Aisin Seiki Kabushiki Kaisha, Kariya-shi (JP)

( * ) Notice: Subject to any disclaimer, the term of this patent is extended or adjusted under 35 U.S.C. 154(b) by 359 days.

(21) Appl. No.: 10/743,734

(22) Filed: Dec. 24, 2003

(65) Prior Publication Data

US 2004/0223159 A1    Nov. 11, 2004

(30) Foreign Application Priority Data

Dec. 24, 2002   (JP)   ............................. 2002-371321
Oct. 23, 2003   (JP)   ............................. 2003-362719

(51) Int. Cl.
*G01N 21/55* (2006.01)
(52) U.S. Cl. ..................................... 356/445
(58) Field of Classification Search .................. None
See application file for complete search history.

(56) References Cited

U.S. PATENT DOCUMENTS

| | | | | |
|---|---|---|---|---|
| 5,898,503 A | * | 4/1999 | Keller et al. ................ | 356/445 |
| 5,923,031 A | * | 7/1999 | Naya ...................... | 250/227.25 |
| 6,692,974 B2 | * | 2/2004 | Perkins ....................... | 436/518 |
| 2002/0127706 A1 | * | 9/2002 | Naya et al. .............. | 435/287.2 |
| 2002/0145737 A1 | * | 10/2002 | Kubo et al. ................. | 356/445 |
| 2003/0128364 A1 | * | 7/2003 | Dickopf et al. ............. | 356/445 |

FOREIGN PATENT DOCUMENTS

| | | |
|---|---|---|
| JP | 9-292333 | 11/1997 |
| JP | 2000-65729 | 3/2000 |

\* cited by examiner

*Primary Examiner*—Michael P. Stafira
(74) *Attorney, Agent, or Firm*—Oblon, Spivak, McClelland, Maier & Neustadt, P.C.

(57) ABSTRACT

A surface plasmon sensor includes a plurality of light supply devices for irradiating a beam, a plurality of surface plasmon resonance detection surfaces where the beam irradiated from the light supply means being incident to, a plurality of light detection devices for detecting the beam reflected at the surface plasmon resonance detection surface, a plurality of reflective surfaces provided at respective optical paths from the light supply devices to the light detection devices, the reflective surfaces being arranged opposing to the respective surface plasmon resonance detection surfaces, a wave formed multiwell formed with the surface plasmon resonance detection surfaces and the reflective surfaces, and the light detection devices positioned close to the light supply means.

19 Claims, 8 Drawing Sheets

SURFACE PLASMON SENSOR, SURFACE PLASMON RESONANCE MEASUREMENT DEVICE, AND DETECTION CHIP

This application is based on and claims priority under 35 U.S.C. § 119 with respect to Japanese Patent Application No. 2003-362719 filed on Oct. 23, 2003, the entire contents of which are incorporated herein by reference.

FIELD OF THE INVENTION

The present invention relates to a surface plasmon resonance measurement device, a surface plasmon sensor, and a detection chip. More particularly, the present invention pertains to a surface plasmon resonance measurement device for detecting and determining the quantity of various materials to be detected at once, a surface plasmon sensor used for the surface plasmon resonance measurement device, and a detection chip used for the surface plasmon sensor.

BACKGROUND OF THE INVENTION

A known surface plasmon resonance measurement device for detecting and determining the quantity of various materials to be detected at once described in Japanese Patent Laid-Open Publication No. 2000-65729 detects a surface plasmon resonance angle (hereafter referred as SPR angle) relative to sample solutions provided in each cell of a cell plate with the following construction. A glass substrate formed with a metal membrane on a first surface thereof is glued at a whole bottom surface of a cell, plate including plural cells. Thereafter a prism is adhered to the glass substrate at a second surface side not provided with the membrane. The known surface plasmon resonance measurement device detects the SPR angle by measuring the light intensity reflected from a boundary surface between the glass substrate and the metal membrane by irradiating the light with a predetermined angular width while adhering the prism to the second side of the glass membrane.

A known surface plasmon resonance measurement device described in Japanese Patent Laid-Open Publication No. 9-292333 includes plural metal membranes formed at a prism. The known surface plasmon resonance measurement device described in Japanese Patent Laid-Open Publication No. 9-292333 detects the SPR angle relative to the sample contacting each metal membrane by irradiating a beam including various incident angle to respective metal membranes to measure the intensity of the beam totally reflected at a boundary of the prism and the metal membranes.

Notwithstanding, with the surface plasmon resonance measurement device described in Japanese Patent Laid-Open Publication No. 2000-65729, it is required to position each cell of the cell plate vis-a-vis the single prism by moving the cell plate manually or with a slider of three dimensional moving mechanism in order to detect and determine the quantity of the minute amount of the material relative to the sample solutions provided in the cells of the cell plate. With this construction, it consumes time for detecting and determining the quantity of the various kinds of the materials to be detected at once.

With the surface plasmon resonance measurement device described in Japanese Patent Laid-Open Publication No. 9-292333, the detection and the determination of the quantity of the various kinds of the materials to be detected requires shorter time than the surface plasmon resonance measurement device described in Japanese Patent laid-Open Publication No. 2000-65729 because the intensity of the reflected beams at the boundary between the prism and the metal membranes can be measured simultaneously by simultaneously irradiating the beams to the respective metal membranes formed at the prism. However, a large space is required for an optical system and a light detection means to function because the optical system for obtaining various angles of the incidence for each beam and the light detection means for detecting the intensity of the beam totally reflected at the boundary between the prism and the metal membranes are positioned on a incident light path and a reflective light path assuming at least two times of the SPR angle in order to detect the SPR signal, which requires the optical system and the light detection means away from each other.

A need thus exists for a surface plasmon resonance measurement device for detecting and determining the quantity of the various materials to be detected at once, a surface plasmon sensor used for the surface plasmon resonance measurement device, and a detection chip used for the surface plasmon sensor, which enable the stable simultaneous detection and the determination of the quantity of the various materials to be detected with low manufacturing cost and enable the reduction in size.

SUMMARY OF THE INVENTION

In light of the foregoing, the present invention provides a surface plasmon sensor, which includes a plurality of light supply means for irradiating a beam, a plurality of surface plasmon resonance detection surfaces where the beam irradiated from the light supply means being incident to, a plurality of light detection means for detecting the beam reflected at the surface plasmon resonance detection surface, a plurality of reflective surfaces provided at respective optical paths from the light supply means to the light detection means, the reflective surfaces being arranged opposing to the respective surface plasmon resonance detection surfaces, a wave formed multiwell formed with the surface plasmon resonance detection surfaces and the reflective surfaces, and the light detection means positioned close to the light supply means.

According to another aspect of the present invention, a surface plasmon resonance measurement device includes a surface plasmon sensor. The surface plasmon sensor includes a plurality of light supply means for irradiating a beam, a plurality of surface plasmon resonance detection surfaces where the beam irradiated from the light supply means being incident to, a plurality of light detection means for detecting the beam reflected at the surface plasmon resonance detection surface, a plurality of reflective surfaces provided at respective optical paths from the light supply means to the light detection means, the reflective surfaces being arranged opposing to the respective surface plasmon resonance detection surfaces, a wave formed multiwell formed with the surface plasmon resonance detection surfaces and the reflective surfaces, and the light detection means positioned close to the light supply means. The surface plasmon resonance measurement device further includes a means for calculating a concentration of targeted ingredient by processing an optical signal from the surface plasmon sensor and a means for communicating with the outside.

According to further aspect of the present invention, a detection chip provided at a surface plasmon sensor includes a multiwell. The detection chip is configured to be detachable relative to an optical unit unitarily including a light supply means and a light detection means.

BRIEF DESCRIPTION OF THE DRAWING FIGURES

The foregoing and additional features and characteristics of the present invention will become more apparent from the following detailed description considered with reference to the accompanying drawing figures in which like reference numerals designate like elements.

DETAILED DESCRIPTION OF THE INVENTION

Figure 1:
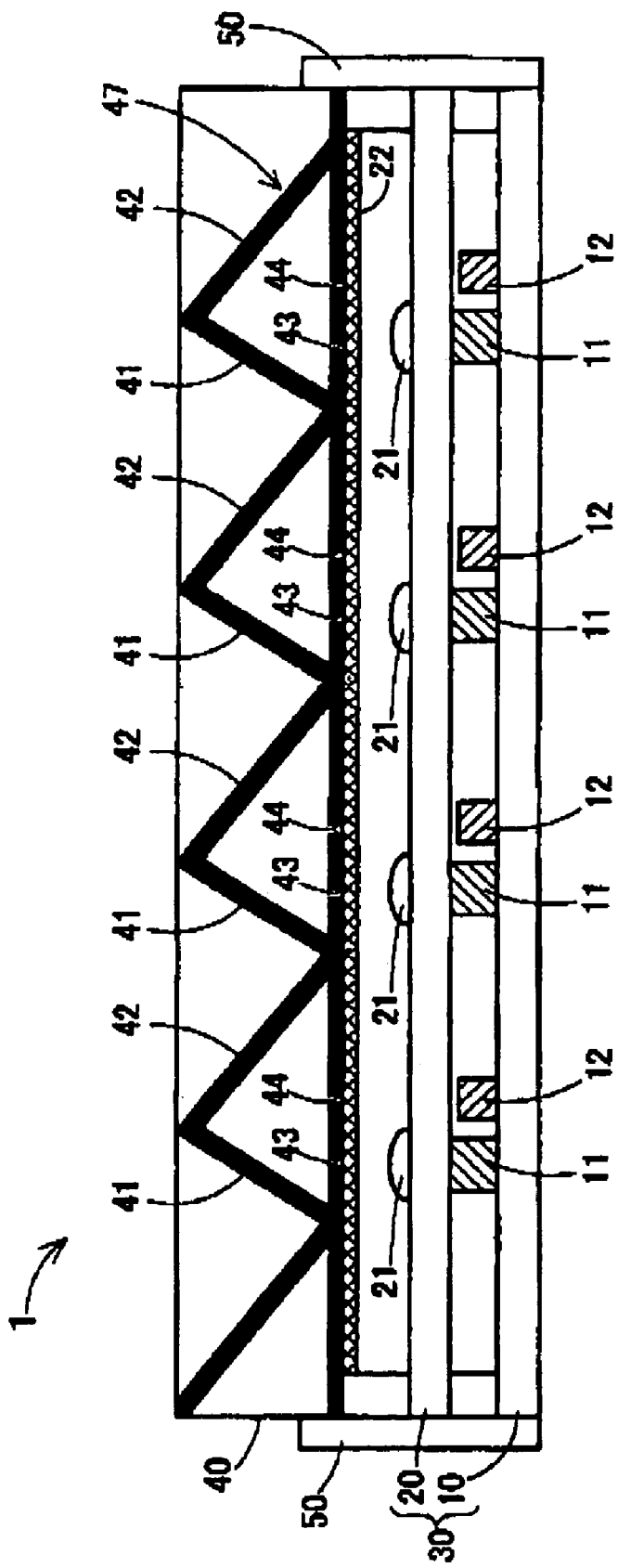
FIG. 1 shows an overview of a surface plasmon sensor according to an embodiment of the present invention.

One embodiment of the present invention will be explained with reference to the illustrations of the drawing figures as follows.

As shown in FIG. 1, a surface plasmon sensor 1 includes an optical unit 30 and a detection chip 40 including a wave shape multiwell 47. The optical unit 30 includes a substrate 10, a lens array 20, and a polarizing filter 22. The substrate 10 is made of a material with high heat transmission for uniformalizing the temperature distribution. Plural pairs of light sources 11 and light receiving portions 12 (12A, 123) are provided at a first plane surface of the substrate 10. The light source 11 and the light receiving portion 12 may be provided on separate substrates to be piled one another. The light source 11 may be a laser diode, a light-emitting diode, or the like, with high monochromatic output. The light receiving portion 12 may be a photo diode, a one-dimensional photo diode array_(linear photodiode array), or the like. The substrate 10 provided with the plural pairs of the light sources 11 and the light receiving portions 12 may be formed by directly manufacturing with a semiconductor process or by pasting a device chip with the high precision positioning, or the like.

Plural lenses 21 made of resin or glass, or the like, are provided at the lens array 20. The lens 21 may be a collimated lens or a focus lens, or the like. The only polarized wave P for resonating the surface plasmon passes through the polarizing filter 22. The polarized wave P is a linear polarized wave whose polarized wave surface is arranged in parallel with a light incident surface to a surface plasmon resonance detection surface (hereafter referred as SPR detection surface) 41.

Connecting the substrate 10, the lens array 20, and the polarizing filter 22 by the positioning with high precision assembles the optical unit 30. A fitting guide 50 is provided at an external peripheral surface of the optical unit 30.

The detection chip 40 includes plural SPR detection surfaces 41, plural reflective surfaces 42, plural first irises 43 (43A, 43B), and plural second irises 44 (44A, 44B). By positioning each SPR detection surface 41 and each reflective surface 42 to be perpendicular to one another alternately, a multiwell 47 is formed. A pair of the first iris 43 and the second iris 44 is formed below each pair of the SPR detection surface 41 and the reflective surface 42 at the detection chip 40.

The wave formed portion of the detection chip 40 is manufactured by die forming the materials such as glass and high polymer with a type with high precision manufactured by LIGA process enabling three-dimensional micro processing. The first irises 43 and the second irises 44 are processed by etching by forming a pattern by the photolithography formed by providing a light shielding membrane at a transparent substrate. The SPR detection surfaces 41 are formed with a metal membrane. An antibody, or the like, for selectively adsorbing the materials to be detected is formed at the metal membrane by inkjet method, or the like, with small amount and high precision.

Figure 2:
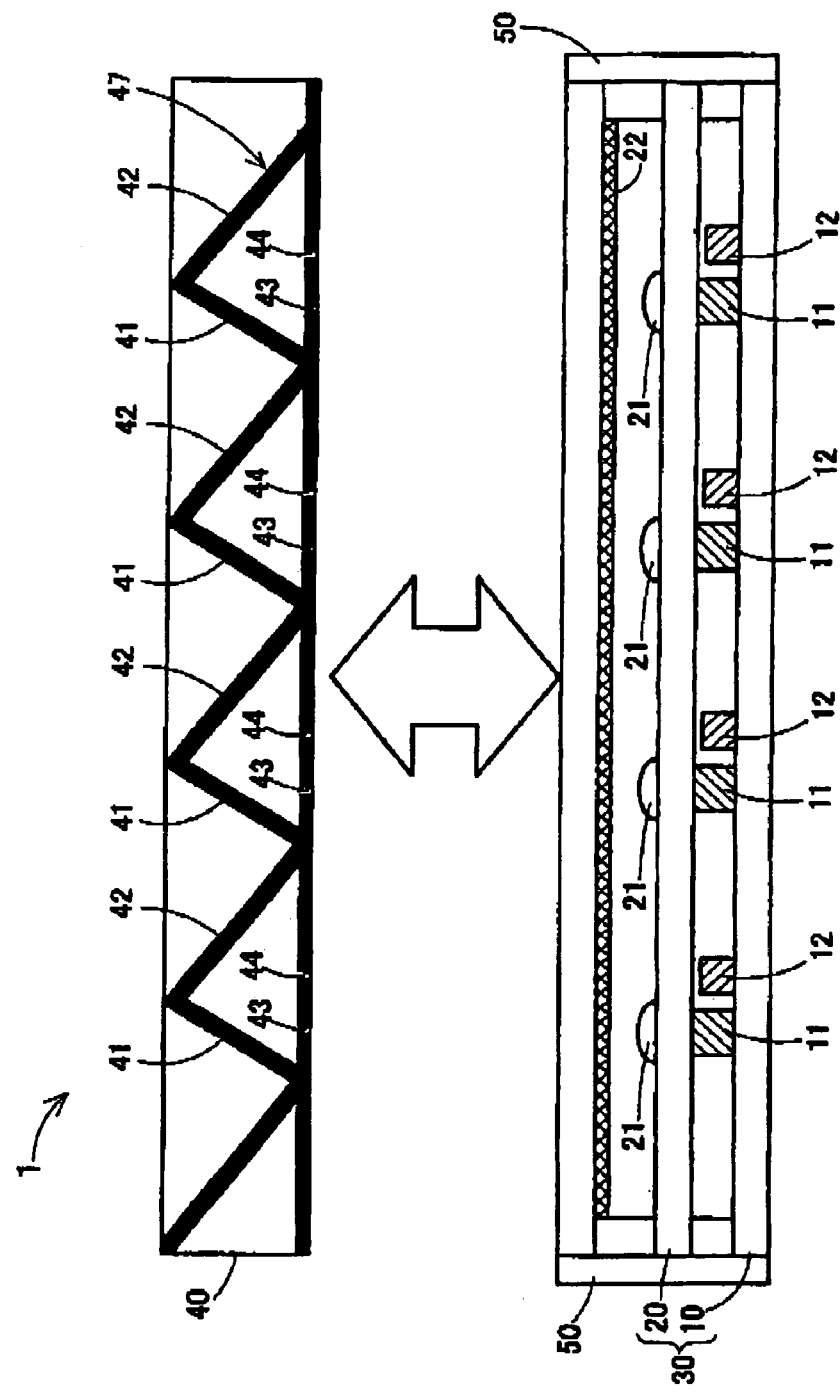
FIG. 2 is the overview of the surface plasmon sensor according to the embodiment of the present invention showing that a multiwell is replaceable relative to an optical unit.

By fitting the detection chip 40 into the optical unit 30 along the fitting guide 50, the surface plasmon sensor 1 is configured. Thus, the surface plasmon sensor 1 of the embodiment is a card type with a simple construction. Further, as shown in FIG. 2, the detection chip 40 is detachable relative to the optical unit 30.

Figure 3:
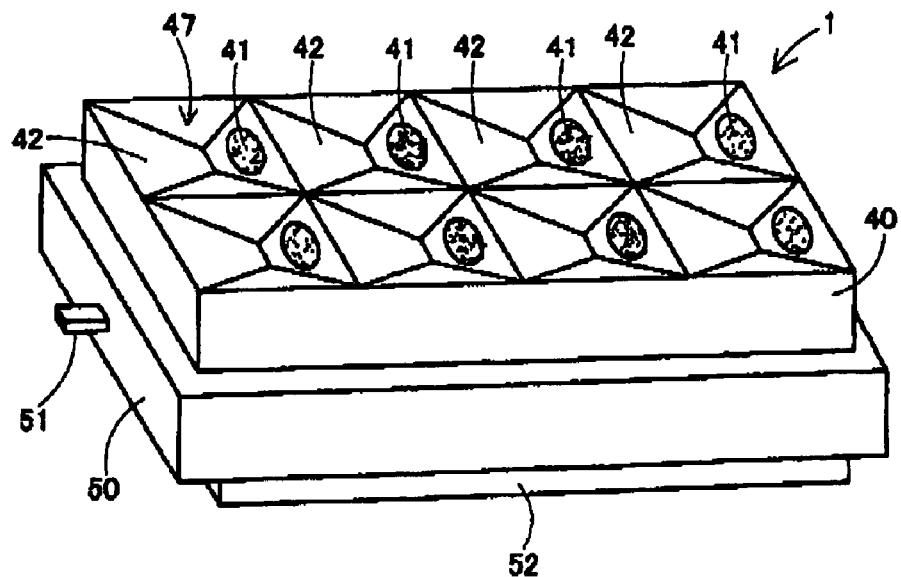
FIG. 3 is a perspective view of the surface plasmon sensor according to the embodiment of the present invention.

As shown in FIG. 3, a temperature compensation device 52 is provided at a bottom of the optical unit 30 covered with the fitting guide 50. The temperature compensation device 52 maintains the temperature of the entire surface plasmon sensor 1 to reduce the change of the wavelength of the light source 11, to reduce the temperature dependence of the light receiving portion 12, and to reduce the temperature dependence of the materials to be detected. Because the substrate 10 is plane, a cooling element such as Peltier element, or the like, is used as the temperature compensation device 52. An input-output micro connector 51 connected to a personal computer 60 (shown in FIG. 8) is provided at a side surface of the fitting guide 50. The personal computer 60 controls the light sources 11 and receives the information from the light receiving portions 12 via the input-output micro connector 51.

With the surface plasmon sensor 1 of the embodiment, samples such as the liquid and the gas can be injected from upward of the detection chip 40 to the respective SPR detection surfaces 41. The sample may be provided to the detection chip 40 by forming a micro conduit at an entire top surface of the detection chip 40. The sample may be provided by providing a wall for each well of the detection chip 40 for injecting the sample, for example, with a dropper.

Figure 6:
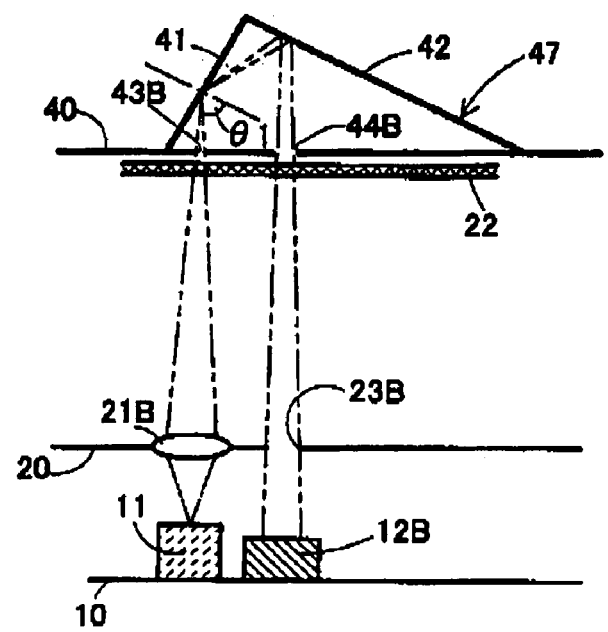
FIG. 6 is a view showing an optical measurement principle when using a focus lens serving as a lens for the leas array at the surface plasmon sensor of the present invention.

The optical measurement principle of the surface plasmon sensor 1 will be explained as follows. As shown in FIG. 6, using a focus lens 21B serving as the lens 21 of the lens array 20, the beam irradiated from the light source 11 assumes a converging light by passing through the focus lens 21B. The converging light assumes only polarized wave P by passing through the polarizing filter 22. The beam immediately after assuming only the polarized wave P passes through the first iris 43B to focus at the SPR detection surface 41 with an angular width including a predetermined value θ1 of the incident angle. Thereafter, the focused beam is totally reflected to forward to the reflective surface 42 arranged having 90 degrees relative to the SPR detection surface 41, The reflective surface 42 and the SPR detection surface 41 may be arranged not to have 90 degrees relative to each other. The beam contacting the reflective surface 42 totally reflects to pass through the second iris 44B, the polarizing filter 22, and a third iris 23B of the lens array 20 in this order to reach the light receiving portion 12B corresponding to a one dimensional photodiode array.

Figure 4:
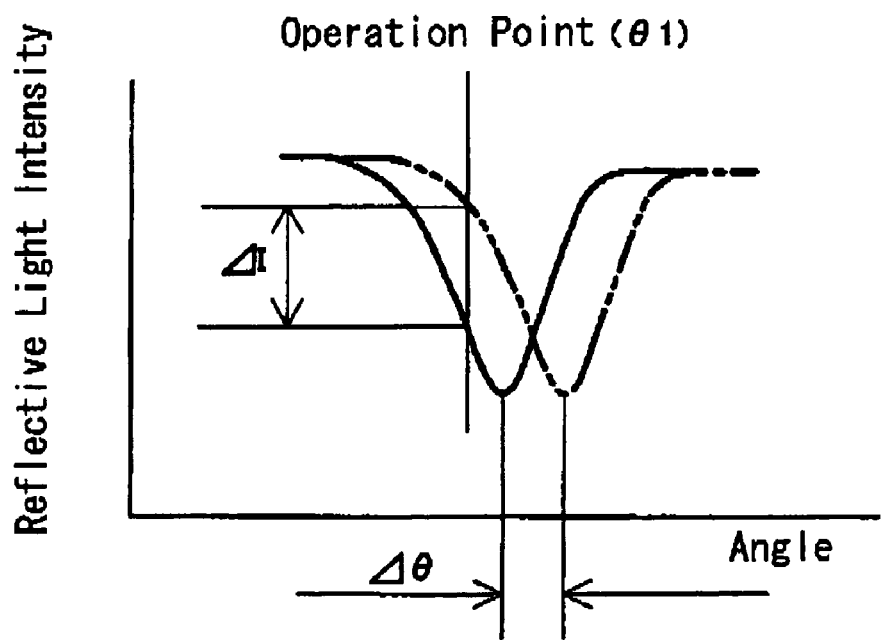
FIG. 4 is a view showing a surface plasmon resonance curve at a surface plasmon resonance detection surface of the surface plasmon sensor according to the embodiment of the present invention.

As shown in FIG. 4, when the antibody, or the like, formed at the mental membrane selectively adsorbs the materials to be detected included in the sample at the SPR detection surface 41, the surface plasmon resonance curve_ (the surface plasmon resonance angle spectrum) moves from an actual line to a two dotted chain line of FIG. 4. The change of the surface plasmon resonance curve (i.e., SPR angle variation Δθ) is detected at the light receiving portion 12B corresponding to the one-dimensional photodiode array. Thus, by sending the detection information of the light receiving portion 12B to the personal computer 60 via the input-output micro connector 51, the material to be detected included in the samples can be detected and the quantity thereof is determined.

Although the detection precision of the change of the surface plasmon resonance curve (i.e., SPR angle variation Δθ) of FIG. 4 is immensely influenced by the resolving power of the light receiving portion 12B for the detection and the determination of the quantity of the materials to be detected included in the sample, the light receiving portion 12B corresponding to the one dimensional photodiode array is selected in accordance with other elements such as the cost and the size. Considering those elements, It is preferable to use the one-dimensional photodiode array having the resolving power, for example, with the number of pixels ranged 128–4096.

Because the foregoing optical measurement principle is processed simultaneously at every wells formed by positioning the SPR detection surface 41 and the reflective surface 42 perpendicularly, the detection and the determination of the quantity of the materials to be detected relative to a numbers of the samples can be processed at once.

A light axis of the beam from the light sources 11 to the respective SPR detection surfaces 41 and the beam from the reflective surface 42 to the light receiving portion 12B are arranged as shown in FIG. 6 for the explanatory purpose. In other words, as shown in FIG. 6, the propagation path of the beam from the reflective surfaces 42 to the light receiving portions 12B is arranged side by side with the propagation path of the beam from the light sources 11 to the SPR detection surfaces 41. The optical measurement principle functions even if the two light axes are not arranged as shown in FIG. 6.

Figure 7A:
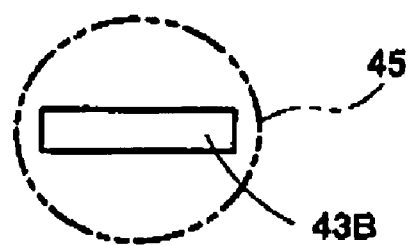
FIG. 7a shows a relationship between an irradiation range of a beam immediately after assuming only polarized wave P and a relative position and size of a first iris slit when using the focus lens as the lens for the lens array at the surface plasmon sensor of the embodiment.

As shown in FIG. 7a, an irradiating range 45 of the beam immediately after assuming the polarized wave P is formed slightly larger than a slit of the first iris 43B in order to ensure the uniformity of the intensity of the beam immediately after assuming only the polarized wave P.

Figure 7B:
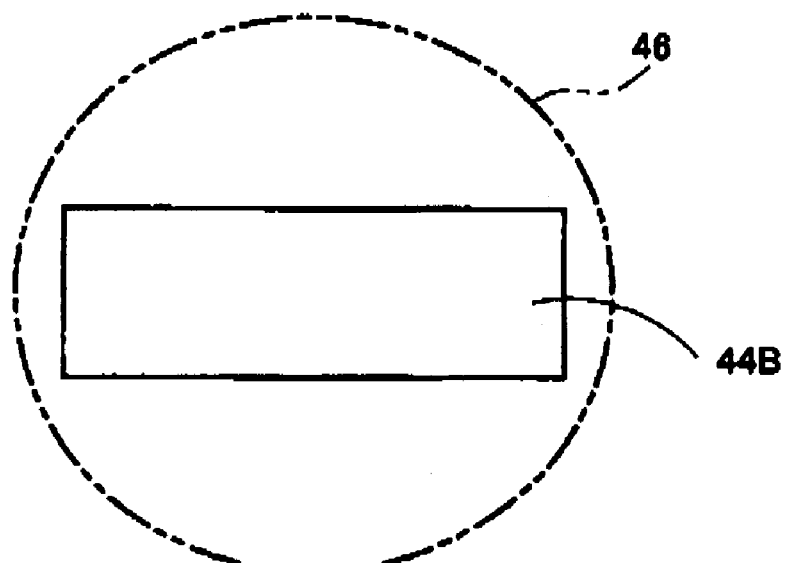
FIG. 7b shows a relationship between an irradiation range of a beam immediately after totally reflecting from a reflection surface and a relative position and size of a second iris slit when using the focus lens as the lens array at the surface plasmon sensor of the embodiment.

As shown in FIG. 7b, an irradiating range 46 of the beam totally reflected from the reflective surface 42 is formed slightly larger than a slit of the second iris 44B in order to ensure the uniformity of the intensity of the beam totally reflected from the reflective surface 42.

Figure 5:
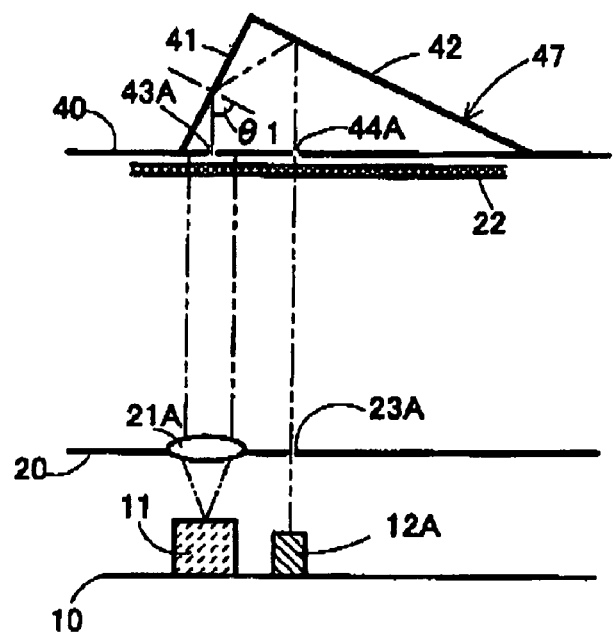
FIG. 5 is a view showing an optical measurement principle when using a collimated lens serving as a lens for a lens array at the surface plasmon sensor of the embodiment of the present invention.

In the meantime, as shown in FIG. 5, the beam irradiated from the light source 11 assumes parallel after passing a collimated lens 21A when using the collimated lens 21A serving as the lens 21 of the lens array 20. Thereafter, the parallel light assumes including only the polarized wave P after passing through the polarizing filter 22. The beam immediately after assuming the polarized wave P assumes a spotlight by passing through the first ids 43A to forward to the SPR detection surface 41. The spotlight reaching the SPR detection surface 41 with a predetermined value θ of the incident angle totally reflects at the SPR detection surface 41 to forward to the reflective surface 42 arranged to have 90 degrees relative to the SPR detection surface 41. The spotlight reaching the reflective surface 42 totally reflects at the reflective surface 42 to pass through the second ids 44A, a polarizing filter 22, and a third iris 23A of the lens array 20, to reach the light receiving portion 12A corresponding to a photodiode having a single element.

As shown in FIG. 4, the surface plasmon resonance curve moves from the actual line, to the two dotted chain line when the antibody formed at the metal membrane selectively adsorbs the materials to be detected included in the sample at the SPR detection surface 41. In order to detect the change of the surface plasmon resonance curve at the light receiving portion corresponding to the photodiode array, data transaction is required. Because an intensity variation ΔI (shown in FIG. 4) of the spotlight totally reflected after reaching the SPR detection surface 41 with a predetermined value θ1 of the incident angle can be detected at the light receiving portion 12A, the detection and the determination of the quantity of the materials to be detected included in the sample is processed by sending the detected information at the light receiving portion 12A to the personal computer 60 via the input-output micro connector 51.

Because the targeted materials to be detected is mostly predetermined for the purpose of the medical diagnosis, or the like, the quantitative detection and the determination of the quantity is sufficiently performed by analyzing the state of the intensity variation ΔI of the spotlight totally reflected after reaching the SPR detection surface 41 with the predetermined value θ1 of the incident angle.

Because the foregoing optical measurement principle is simultaneously processed at every wells formed with the SPR detection sensor 41 and the reflective surface 42 assembled to be perpendicular to each other, the detection and the determination of the quantity of the materials to be detected for various samples and various items can be performed at once.

In this case, the light axis of the beam (i.e., spotlight) from the light source 11 to the SPR detection surface 41 and the light axis of the spotlight from the reflective surface 42 to the light receiving portion 12A is arranged in parallel each other. In other words, the propagation path of the beam (i.e., spotlight) from the light source 11 to the SPR detection surface 41 and the propagation path of the beam from the reflective surface 42 to the light receiving portion 12A are arranged side by side in parallel each other.

Figure 8:
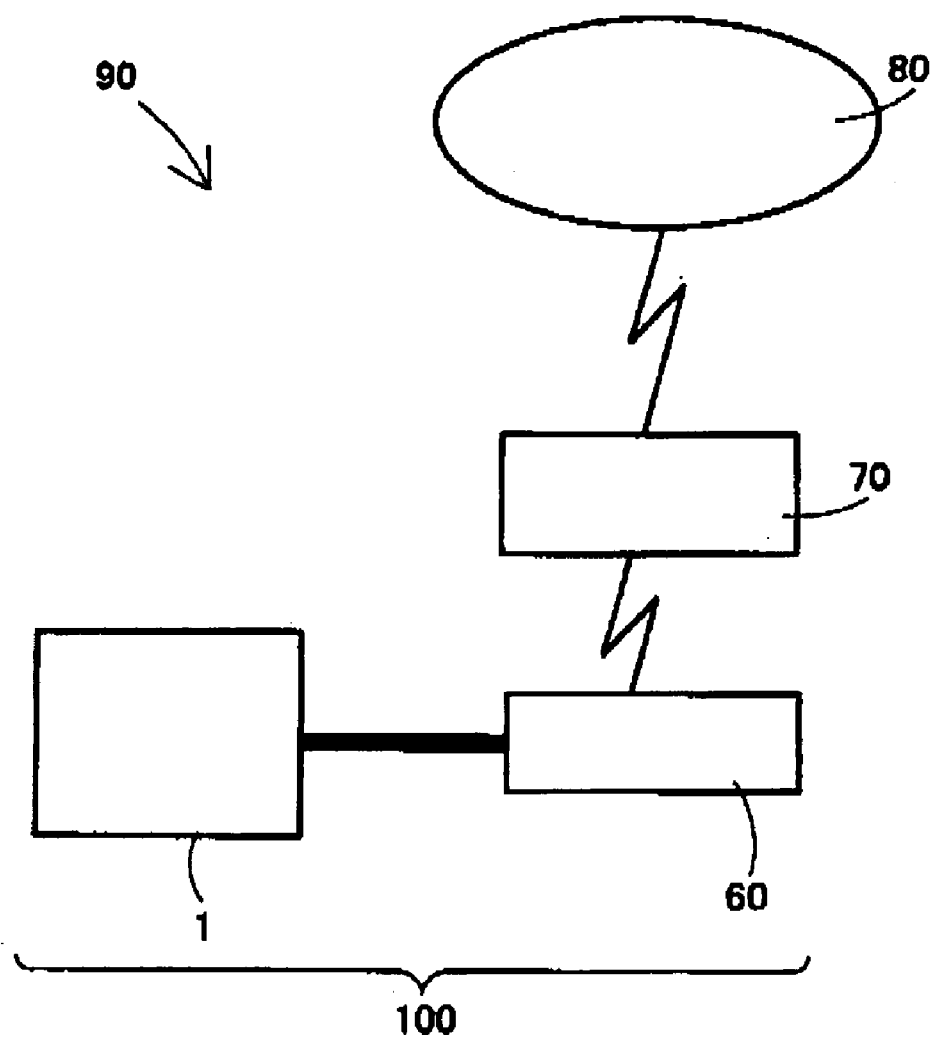
FIG. 8 is an overview showing a connection of the surface plasmon resonance measurement device to an information network according to the embodiment of the present invention.
Figure 9:
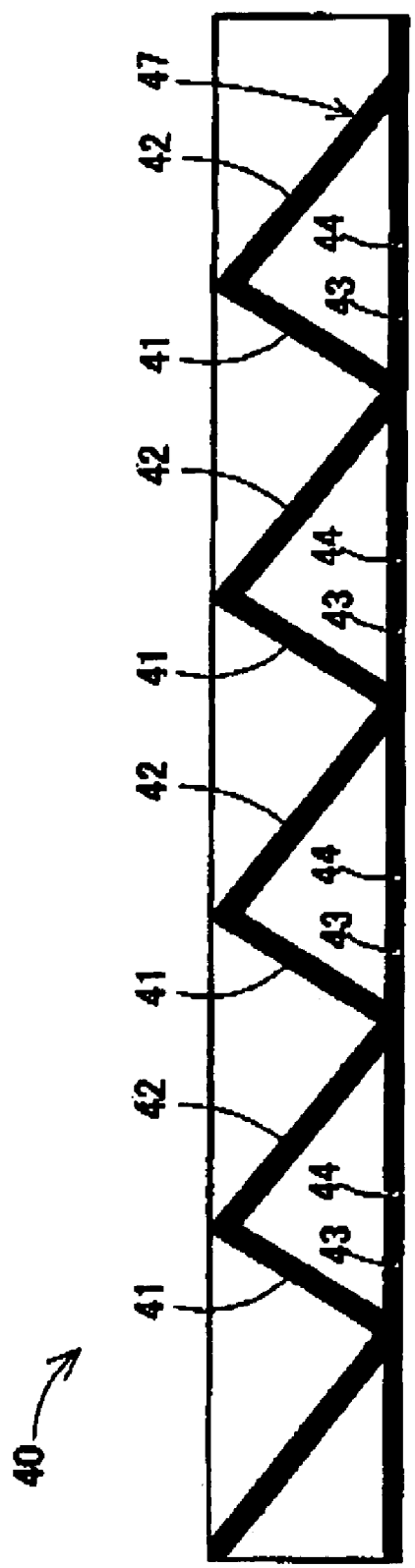
FIG. 9 is an overview showing a detection chip of the surface plasmon sensor according to the embodiment of the present invention.

The surface plasmon resonance measurement device including the surface plasmon sensor 1 of the embodiment will be explained as follows. As shown in FIG. 8, a surface plasmon resonance measurement device 100 includes the surface plasmon sensor 1, the personal computer 60, and the input-output micro connector 51 (shown in FIG. 5). The surface plasmon sensor 1 is connected to the personal computer 60 via the input-output micro connector 51. With the surface plasmon resonance measurement device 100, the detected information simultaneously sent from the plural light receiving portions 12A, 12B (shown in FIGS. 5–6) is analyzed based on the database of various materials memorized in the database to detect and determine the quantity of the materials to be detected for the various samples at once.

By connecting the surface plasmon resonance measurement device 100 to an external database 80 via an Internet 70, various services such as the information analysis, the early discovery of the problems and the countermeasure, and the supply of the software can be obtained. In other words, the surface plasmon resonance measurement device 100 identifies the detected information sent simultaneously from the plural light receiving portions 12A, 12B with the external database 80 to provide a user the result and to discover the problems at the detection of the plural light receiving portions 12A, 12B (shown in FIGS. 5–6) to achieve the early response for the countermeasure.

As explained above, with the surface plasmon sensor 1, the SPR detection surface 41 provides a place for causing the interaction by the biomolecular, or the like, by selectively adsorbing the materials to be detected included in the samples with the antibody formed on the metal membrane. The SPR detection surface 41 serves as a signal transducer for converting the change of the refraction rate deriving from the chemical reaction of a molecule at the SPR detection surface 41 to an SPA signal.

For example, with an immune reaction, when the beam irradiated from the light source 11 enters the SPR detection surface 41 as shown in FIG. 4, the SPR resonance angle of the reflective light moves in accordance with adsorbing the materials to be detected to a first side (i.e., a side that the light is not incident) of the SPR detection surface 41 not provided with the materials to be detected at the SPR detection surface 41 with the specific antigen-antibody reaction. In the meantime, with the SPR detection surface 41 without the specific antigen-antibody reaction, the SPR resonance angle of the reflective light does not move because the first side of the SPR detection surface 41 does not adsorb the materials to be detected. The SPR signal is included in the spotlight or the beam totally reflected at the SPR detection surface 41. Because the spotlight or the beam totally reflected at the SPR detection surface 41 is introduced to the light receiving portions 12A, 12B, the SPR signals from every SPR detection surfaces 41 can be simultaneously obtained.

In this case, the spotlight or the beam totally reflected at the SPR detection surfaces 41 is totally reflected at the reflection surfaces 42 to be introduced to the light receiving portions 12. By forming the wave formed multiwell 47 with the SPR detection surface 41 and the reflective surface 42, each light receiving portion 12 can be positioned close to the light source 11. This enables to reduce the space necessary for functioning the light sources 11 and the light receiving portions 12A, 12B.

The spotlight or the beam totally reflected at the SPR detection surface 41 passes through the propagation path of the spotlight or the beam from the reflective surface 42 to the light receiving portion 12 after entering the reflective surface 42. As shown in FIGS. 5–6, because the SPR detection surface 41 and the reflective surface 42 are arranged alternately to be perpendicular to one another at the wave formed multiwell 47, every propagation paths are arranged to be in parallel one another relative to the propagation paths of the spotlight or the beam from the light sources 11 to the SPR detection surfaces 41 and the light sources 11 and every light receiving portions 12A, 12B are arranged to be side by side one another. Thus, the space required for functioning the light source 11 and the light receiving portions 12A, 12B is reduced.

With the surface plasmon sensor 1, the detection of the intensity of the spotlight or the beam entered (i.e., being incident) or totally reflected at the SPR detection surface 41 at the light receiving portions 12A, 12B is processed relative to the material to be detected provided at the first side of every SPR detection surfaces 41. Thus, the surface plasmon sensor 1 is for detecting and determining the quantity of the various materials to be detected at once. After the beam irradiated from the light sources 11 enters and reflects at the SPR detection surface 41, the spotlight or the beam reflected at the SPR detection surfaces 41 entering at the light receiving portions 12A, 12B respectively via the respective reflective surfaces 42 to send the SPR signal from every SPR detection surfaces 41 simultaneously. This enables the detection and the determination of the quantity of the various materials to be detected By forming the multiwell 47 with the SPR detection surface 41 and the reflective surface 42, the light receiving portions 12A, 12B are arranged close to the light source 11. Tis reduces the space required for functioning the light sources 11 and the light receiving portions 12A, 12B to reduce the total size of the device. Further, with the construction of the embodiments of the present invention, the mechanical driving device for sweeping angle used for known surface plasmon resonance measurement devices is not required, which enables to achieve the stable measurement of the surface plasmon surface resonance with the low cost.

With the surface plasmon sensor 1, the SPR detection surface 41 cannot be reused unless carefully rinsing the every SPR detection surfaces 41 after providing the sample including the material to be detected at the first side of the SPR detection surface 41. Thus, it is desirable to replace the surface plasmon sensor 1 with the clean surface plasmon sensor 1 to ensure the precision of the detection and the determination of the quantity of other materials to be detect d. With the surface plasmon sensor 1, as shown in FIG. 2, the optical unit 30 unitarily including the light sources 11 and the light receiving portions 12 is detachably provided relative to the detection chip 40 including the wave formed multiwell 47 having the SPR detection surfaces 41 and the reflective surfaces 42 via the fitting guide 50. Thus, the detection and determination of the quantity of other materials to be detected can be performed to reuse the optical unit 30 unitarily including the light sources 11 and the light receiving portions 12 only by replacing the detection chip 40.

As shown in FIGS. 5–6, with the surface plasmon sensor 1, the polarizing filter 22 is positioned at the first iris 43 of the detection chip 40 including the multiwell 47 at the light path from the light source 11 to the light receiving portion 12 to enter only the polarized wave P for resonating the surface plasmon to the SPR detection surface 41. Further, by positioning the polarizing filter 22 at the bottom of the second iris 44 of the detection chip 40 having the multiwell 47, the polarizing filter 22 for allowing only the polarized wave P to pass through is positioned at the light path from the light source 11 to the light receiving portion 12. Because the polarized wave S is rarely included in the spotlight to the beam introduced to the light receiving portions 12A, 12B, the light receiving portions 12 detect only the polarized wave P. Thus, the detection and the determination of the quantity of the materials to be detected injected at the first side of the SPR detection surface 41 can be performed with high precision.

With the surface plasmon sensor 1, when the plural focus lenses are provided where the beam irradiated from the light source 11 passing through as the lens 21 of the lens array 20 as shown in FIG. 6, the slit of the first iris 43B is arranged to be inside of the irradiation range 45 of the beam before entering the SPR detection surface 41 (shown in FIG. 7a). The first iris 43B for entering the beam irradiated from the light source 11 only to the desired range relative to the SPR detection surface 41 to reduce the stray light. Thus, even if the beam from the light source 11 is expanded in order to uniform the light intensity of the portion entering the SPR detection surface 41, the beam portion irradiating the position other than the SPR detection surface 41 can be removed at the first iris 43B. Accordingly, the uniformity of the beam entering the SPR detection surface 41 after passing the first iris 43B can be maintained to detect and determine the quantity of the material to be detected provided at the first side of the SPR detection surface 41 with high precision.

Likewise, with the surface plasmon sensor 1, when the plural focus lenses are provided where the beam irradiated from the light source 11 passing through as the lens 21 of the lens array 20 as shown in FIG. 5, the slit of the first iris 43A is arranged to be inside of the irradiation range 45 of the beam before entering the SPR detection surface 41 (shown in FIG. 7a). The first iris 43A for entering the beam irradiated from the light source 11 only to the desired range relative to the SPR detection surface 41 to reduce the stray light. Thus, even if the beam from the light source 11 is expanded in order to uniform the light intensity of the portion entering the SPR detection surface 41, the beam portion irradiating the position other than the SPR detection surface 41 can be removed at the first iris 43A. Accordingly, the uniformity of the beam entering the SPR detection surface 41 after passing the first iris 43A can be maintained to detect and determine the quantity of the material to be detected provided at the first side of the SPR detection surface 41 with high precision.

Figure 10:
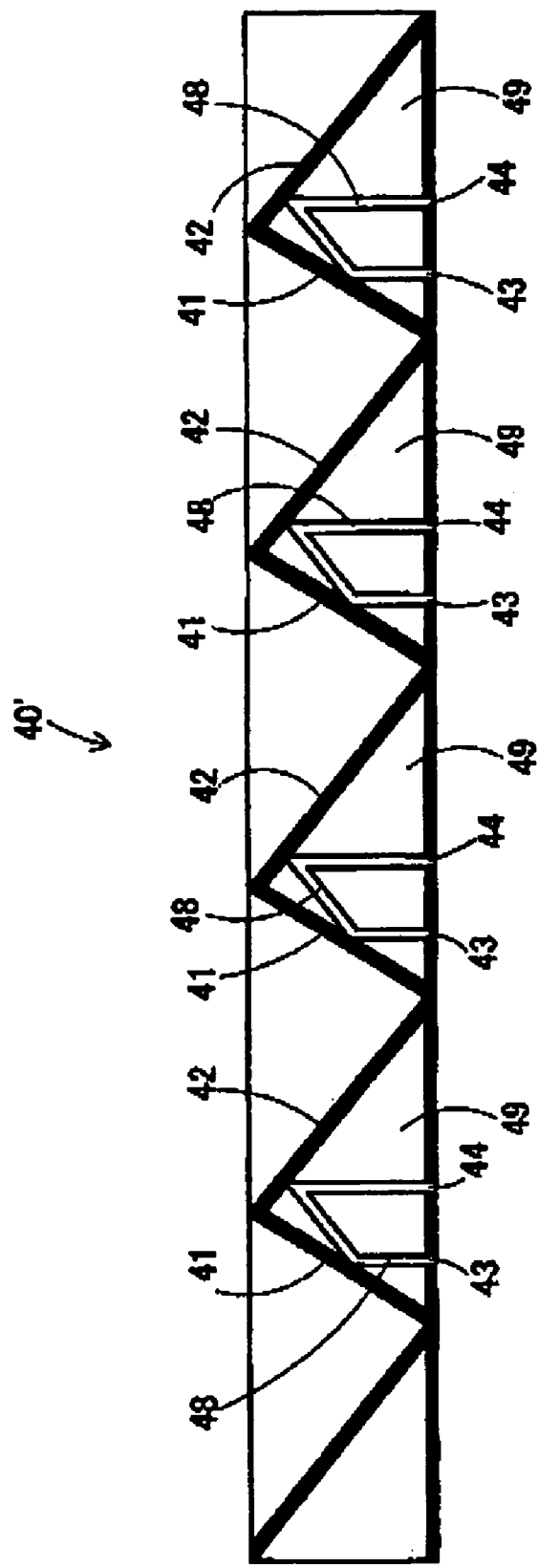
FIG. 10 is an overview of a detection chip including different materials with different refractive index at an optical path and at other portions of the surface plasmon sensor of the embodiment of the present invention.

In the meantime, when the surface plasmon sensor 1 does not include the collimated lens, a detection chip 40' (shown in FIG. 10) may be provided at the surface plasmon sensor in place of the detection chip 40. The detection chip 40' shown in FIG. 10 includes a light transmitting material charged at a portion corresponding to a light path 48 from the iris 43 to the iris 44 and a material to absorb the light charged at a portion 49 other than the light path 48. The detection chip 40' is produced by hardening the portion 49 by charging the light harden resin with different refractive index from the light path 48 after hardening the light path 48 using the light harden resin by irradiating the light thereto. Using the detection chip 40', the only light forwarding straight in accordance with the differences of the refractive index passes through the light path 48 to further reduce the stray light.

With the surface plasmon sensor 1, as shown in FIG. 6, when the lens 21 of the lens array 20 corresponds to the plural focus lens 21B where the beam irradiated from the light source 11 passes through, the slit of the second iris 44B is positioned within the irradiation range 46 of the beam. Thus, the second iris 44B for introducing the beam reflected at the detection surface 41 is provided in order to reduce the stray light to maintain the uniformity of the beam introduced to the light receiving portion 12B via the second iris 44B. Accordingly, the detection and the determination of the quantity of the materials to be detected injected at the first side of the SPR detection surface 41 can be processed with high precision.

Likewise, with the surface plasmon sensor 1, as shown in FIG. 5, when the lens 21 of the lens array 20 corresponds to the plural focus leas 21A where the beam irradiated from the light source 11 passes through, the slit of the second iris 44A is positioned within the irradiation range 46 of the beam. Thus, the second iris 44A for introducing the beam reflected at the detection surface 41 is provided in order to reduce the stray light to maintain the uniformity of the beam introduced to the light receiving portion 12A via the second iris 44A. Accordingly, the detection and the determination of the quantity of the materials to be detected injected at the first side of the SPR detection surface 41 can be processed with high precision.

With the surface plasmon sensor 1, as shown in FIG. 5, the light receiving portion 12A corresponds to the photodiode when the lens 21 of the lens array 20 corresponds to the collimated lens 21A. Among the beam irradiated from the light receiving portion 12A, the beam entering the SPR detection surface 41 with the predetermined angle θ1 having large degree of the angular dependence of the light intensity slightly deviated from the SPR angle (i.e., The light entering the SPR detection surface 41 with the SPR angle rarely reflects at the SPR detection surface among the light being incident from the light source 11 to the SPR detection surface 41. The light assumes more reflective as the incident angle being away from the SPR angle. Thus, the light intensities of the reflective light are immensely different depending on the slight differences of the incident angles.) reflects at the SPR detection surface 41 with the angle θ1 to be detected at a single element of the photodiode corresponding to the light receiving portion 12A. Thus, the intensity variation of the beam of the angle θ1 generated by adsorbing the materials to be detected at the first side of the SPR detection surface 41 can be detected at the light receiving portion 12A. Accordingly, the detection and the determination of the quantity of the materials to be detected supplied to the first side of the SPR detection surface 41 is achieved using a variation ΔI of the intensity of the beam.

With the surface plasmon sensor 1, as shown in FIG. 6, when the lens 21 of the lens array 20 corresponds to the plural focus lenses 21B where the beam irradiated from the light source 11 passing through, one dimensional photodiode array is used for the light receiving portion 12A. Because the beam entering the SPR detection surface 41 with the angle within the range including the SPR angle among the beam irradiated from the light source 11 reflects at the SPR detection surface 41 within the range of the angle to be detected at each element of the one dimensional linear photodiode array corresponding to the light receiving portion 12B, the surface plasmon resonance angle spectrum variation generated by adsorbing the materials to be detected at the first side of the SPR detection surface, in other words, the intensity variation approximate to the resonance angle and the surface plasmon resonance angle variation is detected as the surface plasmon resonance curve of FIG. 4. Thus, using the variation (SPR angle variation Δθ) when the surface plasmon resonance curve moves from the actual line to the two dotted chain line, the detection and the determination of the quantity of the materials to be detected supplied to the first side of the SPR detection surface 41 can be achieved.

With the surface plasmon resonance measurement device 100, as shown in FIG. 8, by analyzing the detected information sent simultaneously from the plural light receiving portions 12A, 12B (shown in FIGS. 5–6) using the database of various materials, the detection and the determination of the quantity of the materials to be detected relative to the various samples can be achieved at once. The surface plasmon resonance measurement device 100 is connected to the external database 80 via the Internet 70. Thus, the surface plasmon resonance measurement device 100 includes the function to calculate the concentration of the objective ingredient by processing the optical signal obtained from the surface plasmon sensor 1 and the function to communicate with outside. Further, because the surface plasmon sensor 1 is capable of processing the detection and the determination of the quantity of the various materials to be detected at once and the total size thereof is reduced, the surface plasmon resonance measurement device 100 per se is reduced in size and is capable of detecting and determining the quantity of the various materials to be detected simultaneously.

Because the detection chip 40 is detachable relative to the optical unit 30, replacing the used detection chip 40 once supplied with the materials to be detected at the first side of the all SPR detection surfaces 41 of the multiwell 47 with the new detection chip 40 is advantageous for proceeding the detection and for the precision of the detection and the determination of the quantity of the materials to be detected.

Although the lenses of the lens array 20 corresponds to the plural collimated lenses 21A where the beam irradiated from the light source 11 passing through as shown in FIG. 5, the collimated lenses 21A may be omitted if the beam irradiated from the light source 11 includes the directional characteristics.

Although the first iris 43 and the second iris 44 are provided at the detection chip 40 as shown in FIGS. 1–2, the first iris 43 and the second iris 44 may be provided at the optical unit 30.

Although the polarizing filter 22 is provided at the bottom of the first iris 43 and the second iris 44 as shown in FIGS. 1–2, with the surface plasmon sensor 1 of the embodiment, the polarizing filter 22 may be provided only at the bottom of the first iris 43.

With the surface plasmon sensor 1 of the embodiment, the third irises 23A, 23B (shown in FIGS. 5–6) may include the function of the second iris 44B of FIG. 6.

With the surface plasmon sensor 1 of the embodiment, the predetermined value θ1 may be different at every SPR detection surfaces 41, may be the same at some SPR detection surfaces 41, and may be the same at the all SPR detection surfaces 41 because the surface plasmon sensor 1 is produced by predetermining the light incident angle θ1 of the beam or the spotlight entering the SPR detection surface 41 in accordance with the variations of the materials to be detected for simultaneously detecting and determining the quantity of the materials to be detected. Further, the antibody, or the like, on the metal membrane may be different at the all SPR detection surfaces 41, may be the same at some SPR detection surfaces 41, and may be the same at the all SPR detection surfaces 41 because the antibody, or the like, selectively adsorbing the materials to be detected is formed on the metal membrane in accordance with the variations of the materials to be detected for simultaneously detecting and determining the quantity of the materials to be detected.

With the surface plasmon sensor 1 of the embodiment, the polarizing filter 22 may be omitted if the light source 11 provides the beam including the linear polarized wave (polarized wave P) whose polarized wave surface is in parallel with the light incident surface relative to the SPR detection surface 41. For this purpose, for example, a diode including a small polarizing filter having the identical function with the polarized filter 22 may be used as the light source 11.

Although the lens 21 for effectively entering the beam irradiated from the light source 11 to the SPR detection surface is provided at the outside of the light source 11 with the surface plasmon sensor 1 of the embodiment, the lens 21 may be provided inside of the light source 11. Although the lens 21 may be defined for effectively introducing the beam irradiated at the SPR detection surface 41 to the light receiving portion 12, additional lens for effectively introducing the beam irradiated at the SPR detection surface 41 may be provided and the lens may be provided inside of the light receiving portion 12.

The principles, preferred embodiment and mode of operation of the present invention have been described in the foregoing specification. However, the invention which is intended to be protected is not to be construed as limited to the particular embodiment disclosed. Further, the embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. A surface plasmon sensor comprising:
    a plurality of light supply means for irradiating a beam;
    a plurality of surface plasmon resonance detection surfaces where the beam irradiated from the light supply means being incident to;
    a plurality of light detection means for detecting the beam reflected at the surface plasmon resonance detection surface;
    a plurality of reflective surfaces provided at respective optical paths from the light supply means to the light detection means, the reflective surfaces being arranged opposing to the respective surface plasmon resonance detection surfaces;
    a wave formed multiwell formed with the surface plasmon resonance detection surfaces and the reflective surfaces; and
    the light detection means positioned close to the light supply means.

2. The surface plasmon sensor according to claim 1, wherein the wave formed multiwell is formed by arranging each said surface plasmon resonance detection surfaces and each said reflective surface alternately to be perpendicular to one another.

3. The surface plasmon sensor according to claim 1, further comprising:
    an optical unit unitarily including the light supply means and the light detection means; and
    a detection chip including the multiwell, the detection chip detachably provided at the optical unit.

4. The surface plasmon sensor according to claim 3, wherein the detection chip includes an optical path and another portion charged with a material with a different refractive index from a material charged at the optical path.

5. The surface plasmon sensor according to claim 1, wherein the light detection means includes a single element photodiode;
the single element photodiode detects intensities of the beam with a predetermined reflective angle, so that the surface plasmon sensor detects the materials to be detected by analyzing the state of the intensity variation of the beam with a predetermined reflective angle.

6. The surface plasmon sensor according to claim 1, wherein
the light detection means includes a linear photodiode array;
the linear photodiode array detects the beams with variable reflective angles reflected at the surface plasmon resonance detection surface to detect a change of a surface plasmon resonance curve.

7. The surface plasmon sensor according to claim 1, further comprising a polarizing filter for allowing only a polarized wave P to pass through.

8. The surface plasmon sensor according to claim 1, wherein the light supply means and the light detection means are positioned at an identical plane surface.

9. A surface plasmon resonance measurement device comprising:
a surface plasmon sensor, the surface plasmon sensor comprising a plurality of light supply means for irradiating a beam;
a plurality of surface plasmon resonance detection surfaces where the beam irradiated from the light supply means being incident to;
a plurality of light detection means for detecting the beam reflected at the surface plasmon resonance detection surface;
a plurality of reflective surfaces provided at respective optical paths from the light supply means to the light detection means, the reflective surfaces being arranged opposing to the respective surface plasmon resonance detection surfaces;
a wave formed multiwell formed with the surface plasmon, resonance detection surfaces and the reflective surfaces;
the light detection means positioned close to the light supply means;
a means for calculating a concentration of targeted ingredient by processing an optical signal from the surface plasmon sensor; and
a means for communicating with the outside.

10. The surface plasmon resonance measurement device according to claim 9, wherein the wave formed multiwell is formed by arranging each said surface plasmon resonance detection surfaces and each said reflective surface alternately to be perpendicular to one another.

11. The surface plasmon resonance measurement device according to claim 9, wherein the surface plasmon sensor further comprises:
an optical unit unitarily including the light supply means and the light detection means; and
a detection chip including the multiwell, the detection chip detachably provided at the optical unit.

12. The surface plasmon resonance measurement device according to claim 9, wherein the detection chip includes an optical path and another portion charged with a material with a different refractive index from a material charged at the optical path.

13. The surface plasmon resonance measurement device according to claim 9, wherein the light detection means includes a single element photodiode;
the single element photodiode detects intensities of the beam with a predetermined reflective angle, so that the surface plasmon sensor detects the materials to be detected by analyzing the state of the intensity variation of the beam with a predetermined reflective angle.

14. The surface plasmon resonance measurement device according to claim 9, wherein
the light detection means includes a linear photodiode array; and
the linear photodiode array detects the beams with variable reflective angles reflected at the surface plasmon resonance detection surface to detect a change of a surface plasmon resonance curve.

15. The surface plasmon resonance measurement device according to claim 9, further comprising a polarizing filter for allowing only a polarized wave P to pass through.

16. A detection chip provided at the surface plasmon sensor according to claim 1, wherein the detection chip is configured to be detachable relative to an optical unit unitarily including the light supply means and the light detection means.

17. The detection chip according to claim 16 further comprising:
a light path charged with a first material; and
another portion charged with a second material having a different refractive index from the first material.

18. A detection chip provided at the surface plasmon resonance measurement device according to claim 9, wherein the detection chip is configured to be detachable relative to an optical unit unitarily including the light supply means and the light detection means.

19. The detection chip according to claim 18, further comprising:
a light path charged with a charged with a first material; and
another portion charged with a second material having a different refractive index from the first material.

* * * * *